(12) United States Patent
Taweh (10) Patent No.: US 10,533,308 B2
(45) Date of Patent: Jan. 14, 2020

(54) DIALYSIS WALL BOX APPARATUS AND WALL CHASE SYSTEM

(71) Applicant: George Taweh, Farmington, CT (US)

(72) Inventor: George Taweh, Farmington, CT (US)

(73) Assignee: George Taweh, Farmington, CT (US)

( * ) Notice: Subject to any disclaimer, the term of this patent is extended or adjusted under 35 U.S.C. 154(b) by 218 days.

(21) Appl. No.: 15/845,519

(22) Filed: Dec. 18, 2017

(65) Prior Publication Data

US 2019/0186110 A1    Jun. 20, 2019

(51) Int. Cl.
| | |
|---|---|
| *E03C 1/02* | (2006.01) |
| *A61M 39/10* | (2006.01) |
| *E04C 2/52* | (2006.01) |
| *A61M 1/14* | (2006.01) |
| *A61M 1/16* | (2006.01) |

(52) U.S. Cl.
CPC .......... *E03C 1/021* (2013.01); *A61M 39/105* (2013.01); *E03C 1/025* (2013.01); *A61M 1/14* (2013.01); *A61M 1/1656* (2013.01); *A61M 2209/084* (2013.01); *E04C 2/521* (2013.01)

(58) Field of Classification Search
None
See application file for complete search history.

(56) References Cited

U.S. PATENT DOCUMENTS

| | | | | |
|---|---|---|---|---|
| 3,934,605 A | * | 1/1976 | Legris | F16L 37/26 |
| | | | | 137/271 |
| 5,282,488 A | * | 2/1994 | Roth | B67D 7/78 |
| | | | | 137/15.08 |
| 8,496,029 B2 | * | 7/2013 | Vu | F16L 41/03 |
| | | | | 137/271 |
| 9,421,312 B1 | | 8/2016 | Marinan et al. | |
| 2010/0140149 A1 | | 6/2010 | Fulkerson | |
| 2015/0314056 A1 | | 11/2015 | Giordano et al. | |

* cited by examiner

*Primary Examiner* — Krishnan S Menon
(74) *Attorney, Agent, or Firm* — Emanus, LLC; Willie Jacques (57) ABSTRACT

A wall box apparatus and building wall chase system is described. A wall box apparatus is configured to operatively reduce the number of fluid line joints connected to building and machinery plumbing lines, and more particularly to dialysis treatment facilities and kidney-dialysis machines, respectively. A space-saving wall chase system is configured using the wall box to connect plumbing lines in a dialysis treatment facility to dialysis machines.

23 Claims, 8 Drawing Sheets

DIALYSIS WALL BOX APPARATUS AND WALL CHASE SYSTEM

BACKGROUND OF THE INVENTION

This invention relates to providing an improved building wall chase system and a wall box apparatus for routing and connecting to, respectively, plumbing lines within the interior of a new or existing building structure and machines within the building. More particularly, this invention relates to providing a wall chase system and wall box apparatus within the interior of a specialty medical treatment facility (e.g., kidney-dialysis treatment facility).

Contemporary kidney-dialysis treatment facilities include groupings of multiple kidney-dialysis machines located at a designated station within a common treatment room. Each station includes a kidney-dialysis machine configured to receive treated water (e.g., Reverse Osmosis (RO) or Deionized (DI) water), acid concentrates, and bicarbonate concentrates dialysate, electrical power, etc., and waste-fluid disposal via a wall-box and wall chase system. Contemporary wall-boxes such as those manufactured by companies like Perma-Chase, Whitehall Manufacturing and WD Manor Mechanical Contractors provide panel-mounted shut-off valves and fittings for various connections to kidney-dialysis machine plumbing lines and drain line. The wall boxes are housed within chase systems for protectively containing plumbing lines, fittings such as valves, and other plumbing connections, where such chase systems sit offset from the interior walls of a treatment room. Such chase systems require substantial treatment facility floor space and, as such, increase real estate and construction capital costs of building structures utilizing them. Industry literature describes chase systems, even those with recessed wall boxes, as being designed to afford more work space and prevent damage to valves and dialysis machine connections when chairs recline. In an exemplary chase system disclosed in U.S. Pat. No. 9,421,312 to Marinan, Aug. 23, 2016, each station, comprised of standard-sized chase system components, typically require about 9 square feet of floor space and 24 cubic feet of volume. Clearly, an improved wall chase system that efficiently reduces kidney-dialysis treatment facilities space requirements (i.e., real estate costs) for supplying plumbing lines to kidney-dialysis stations while also reducing construction costs for chase wall millwork is desirable.

In addition, present-day kidney-dialysis wall boxes are comprised of numerous plumbing fitting interfaces (i.e., joints) created through plumbing connections between a building structure's plumbing lines (i.e., loops), building waste lines and fluid plumbing lines of kidney-dialysis machines. The more such joints are created, the greater the chance of fluid leaks and bacterial growth, thereby resulting in an increased need for disinfection and maintenance. U.S. Pat. No. 9,421,312 to Marinan, Aug. 23, 2016 discloses a typical fluid collector (i.e., wall box) that is comprised of numerous joints (i.e., points where fittings, including valves, plumbing lines, and valve disconnects, etc. are joined together). Marinan further discloses that it is well established that such leakages promote the development of mold, may produce other health risks associated with the presence of persistent moisture, and can cause costly damage to the affected building components. Such costs and associated financial burden are borne by dialysis treatment facility builders and operators who have a desire to reduce such financial burden. Therefore, there is a need in the art for a dialysis wall box and wall box chase system that addresses such deficiencies present in the prior art wall boxes.

OBJECTS AND FEATURES OF THE INVENTION

Accordingly, several objects and advantages of present invention are to provide an integrated and more effective (e.g., disinfection management) wall box which also lends itself to use of a smaller wall chase system addressing the above-mentioned needs. It is a further object and feature of the present invention to provide a wall box that is comprised of fluid flow conduits and connecting ports that effectively reduces the number of plumbing line connection joints, as a way to minimize bacterial growth sites and plumbing leaks. It is another object and feature of the present invention to construct a wall box of materials compatible and homogeneous with current kidney-dialysis treatment facilities' piping, such as PEX, in order to maintain sterility of the treatment facility's plumbing system. It is still a further object and feature of the present invention to provide a wall box comprised of fluid flow conduits effectively sized and of sufficient strength to transport fluid flow through building and kidney-dialysis machine plumbing lines. Such a wall box may be constructed at a substantially smaller footprint than prior art wall boxes while still maintaining fluid pressure containment requirements. Another object of the present invention is to provide a wall box of an alternate configuration having an overall manufactured dimension that is substantially smaller than prior art wall boxes and, as such, reducing the space requirements for a wall chase system. It is a further object and feature of the present invention to provide a separate waste collector for receiving kidney-dialysis machine fluid wastes, providing additional safeguard against wall box leaks, and routing such wastes directly to a building structure's drain line thereby eliminating the need for treatment facility floor sinks. Likewise, another object and feature of the present invention is to provide a wall chase system that enables separately locating a building structure's electrical connections, data lines, and the like away from proximity to plumbing fluid lines. Further objects and features of the present invention will become apparent from a consideration of the drawings and ensuing description.

SUMMARY OF THE INVENTION

In accordance with an embodiment hereof, the present invention provides a wall box apparatus for connecting to loops of a kidney-dialysis treatment facility and plumbing lines of kidney-dialysis machines. Exemplary aspects of the wall box (e.g., machined internal conduits) reduce the number of joints required to connect to dialysis treatment facilities' loops and kidney-dialysis machines' plumbing connections. In an exemplary embodiment, the wall box is made of PEX (crosslinked polyethylene) to be compatible with sterility properties of current piping material used in kidney-dialysis treatment facilities. A further aspect of the present invention is to provide a wall box that eliminates the need for at least one T-joint and at least one fitting used for connecting a wall box to kidney-dialysis treatment facility loops and/or plumbing lines of a kidney-dialysis machine. In another aspect of the present invention, a wall box, comprised of internal conduits, may be constructed of a minimal size sufficient to receive loops and fluid plumbing lines while still containing fluid pressures therein. A further aspect of the present invention is to provide a funnel means, separate of a wall box, for receiving waste fluid from a kidney-dialysis machine, capturing fluid leaks from a wall box, and channeling the fluids and wastes directly to a treatment facility's drain line. The aforementioned aspects of the present invention (e.g., wall box, loops, etc.) are optionally covered and protected by a wall chase system, such as a bumper guard rail, that substantially reduces the amount of facility floor space and room volume required to contain wall boxes, loops, and dialysis machine fluid lines. In accordance with an embodiment hereof, this invention provides a dialysis wall-box and chase system that is more compact and effective than current wall box and chase systems.

BRIEF DESCRIPTION OF THE DRAWINGS

While the specification concludes with claims particularly pointing out and distinctly claiming particular embodiments of the instant invention, various embodiments of the invention can be more readily understood and appreciated from the following descriptions of various embodiments of the invention when read in conjunction with the accompanying drawings in which:

DETAILED DESCRIPTION OF THE INVENTION

Reference will now be made in detail to specific embodiments or features, examples of which are illustrated in the accompanying drawings. Wherever possible, corresponding or similar reference numbers will be used throughout the drawings to refer to the same or corresponding parts. Moreover, references to various elements described herein, are made individually or collectively when there may be more than one element of the same type. However, such references are merely exemplary in nature. It may be noted that any reference to elements in the singular may also be construed to relate to the plural and vice-versa without limiting the scope of the disclosure to the exact number or type of such elements unless set forth explicitly in the appended claims.

Figures 1A, 1B:
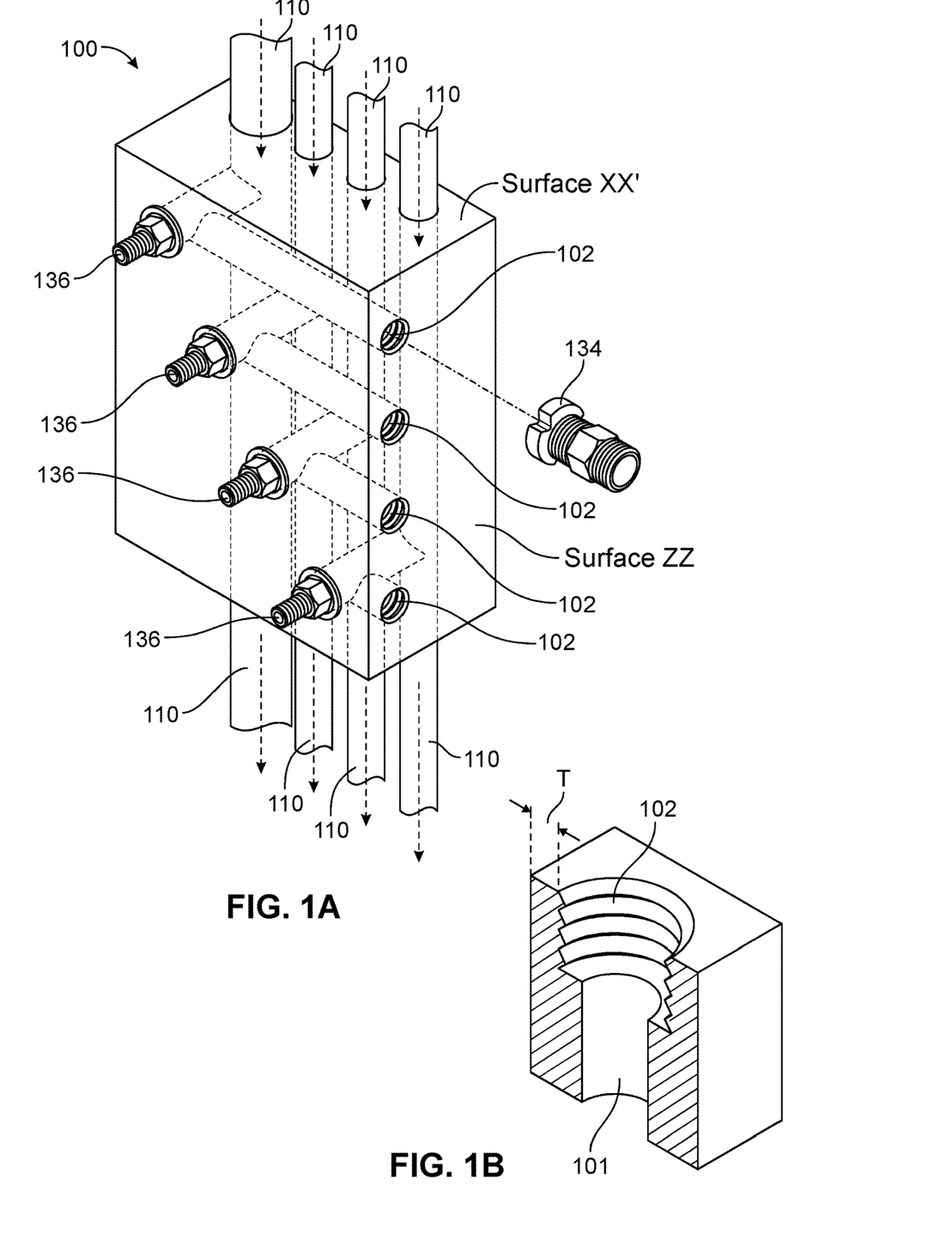
FIG. 1A is a perspective view of a wall box apparatus, in accordance with an embodiment of the present disclosure.
FIG. 1B is a perspective sectional view of a fluid flow conduit and connecting port of a wall box apparatus, in accordance with an embodiment of the present disclosure.

FIG. 1A illustrates an embodiment of the present invention wall box 100. The exemplary wall box 100 is a fluid transport housing generally constructed of PVC (polyvinyl chloride) or PEX (crosslinked polyethylene) material, and having exemplary overall dimensions of approximately 7.0"×3.0"×5.0" (box shape); however, it is contemplated that the wall box 100 may have any other dimensions, or suitable shape, such as cylindrical, hexagonal, etc. Use of PEX allows wall box 100 to be compatible with current pipe tubing material used in kidney-dialysis treatment facilities, thereby providing homogeneous sterility for the wall box 100 and a facility's piping system. However, wall box 100 may be constructed of materials other than PVC or PEX. Furthermore, exemplary wall box 100 may be constructed by machining, molding, sonic welding, thermal press, or other suitable construction means.

Referring to FIGS. 1A and 1B, exemplary wall box 100 may be constructed of any material and have minimum dimensions configured to have sufficient strength to withhold fluid flow pressure therethrough. Fluid flow conduits 101, extending from connecting ports 102, are fluid transport holes machine drilled or otherwise formed (e.g., separately molded components of wall box 100, electrical discharge machining, etc.) within exemplary wall box 100. As an example, overall dimensions of wall box 100 may be sized such that fluid lines 101 have minimum wall thickness "T" to withhold internal pressure of fluids being transported therethrough. The overall dimensions of exemplary wall box 100 are constrained, only by the thinnest wall thickness (e.g., "T") adjacent fluid flow conduits 101 and connecting ports 102.

A fluid flow conduit 101 may terminate without a corresponding connecting port 102 on Surfaces XX, XX', YY, and ZZ, representing the left side, right side, front side, and bottom side of wall box 100, respectively. For the sake of clarity, Surface XX and Surface XX' are on opposite faces of wall box 100. Fluid flow conduit 101 or connecting port 102 may be fashioned as straight diameter holes, conical holes, chamfered holes or other suitable shape; or configured as smooth, threaded, notched or other construction suitable for connecting to loops, plumbing lines, valves, or fittings, respectively. Fluid flow conduits 101 may be straight, curved or otherwise configured, and may be smooth, threaded, or otherwise finished for connecting to other internal fluid flow conduits 101. It is contemplated that wall box 100 may be configured with one or more fluid flow conduits 101 configured with/without connecting port 102 terminating on surfaces XX, XX', YY, and ZZ.

Connecting ports 102 may be counterbored/countersunk, straight, curved or may be otherwise configured at surfaces XX, XX', YY, and ZZ, and may be smooth, threaded, or otherwise finished for connecting to plumbing lines, pipes, fittings, etc. as commonly known in the plumbing art. In accordance with an embodiment of the present disclosure, and by reference to FIGS. 1A, 3A, and 3C surface YY shows plumbing fittings configured as flow control valves 136 for regulating the flow of dialysis treatment fluids (e.g., RO or DI water, acid concentrates, bicarbonate concentrates dialysate, etc.) between loops 110 and a kidney dialysis machine (not shown) via plumbing lines 120.

Figure 2A:
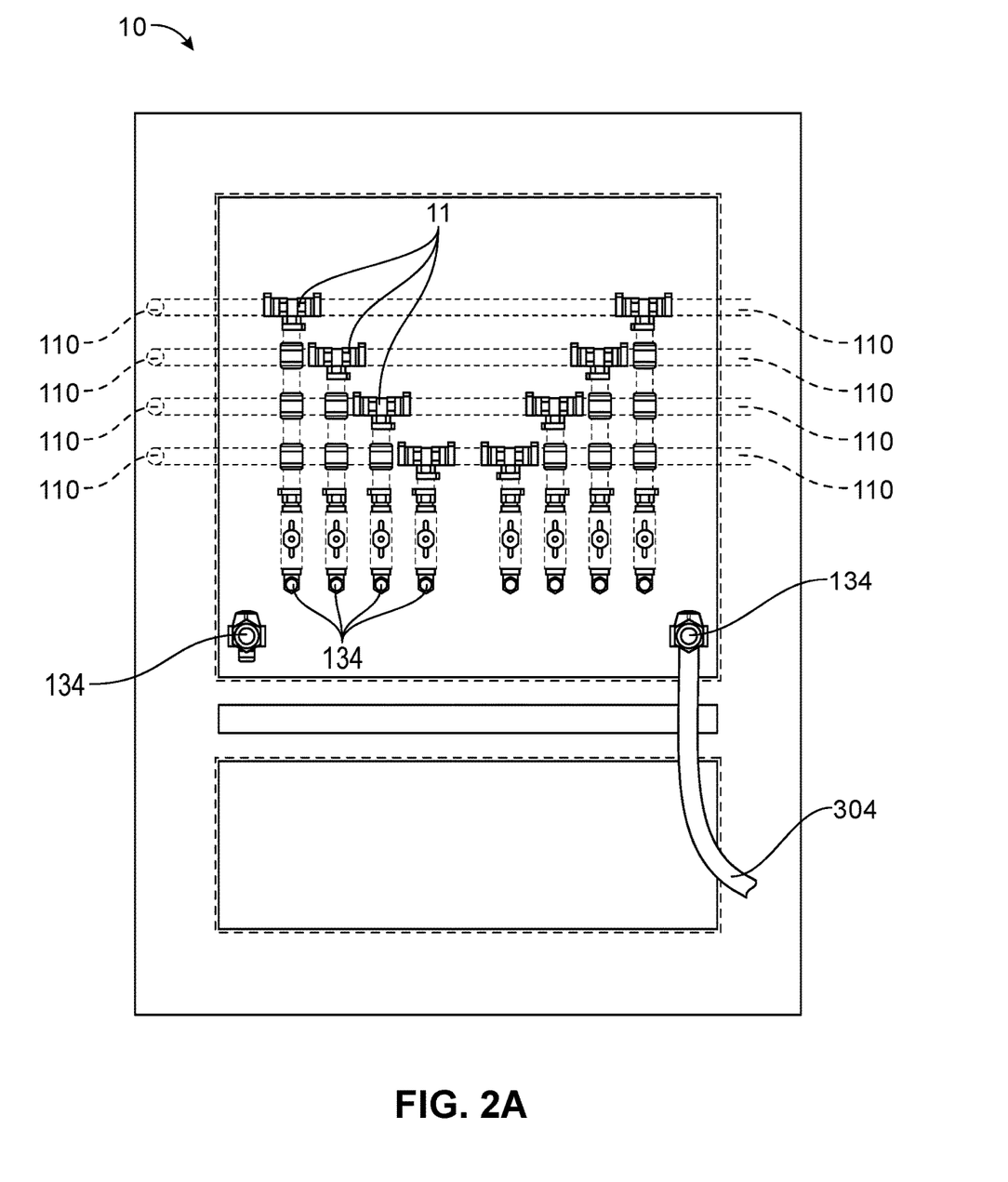
FIG. 2A shows a front elevational view, illustrating a plurality of loops, fluid plumbing lines, T-joints, and fittings of a prior art dialysis wall box.
Figure 2B:
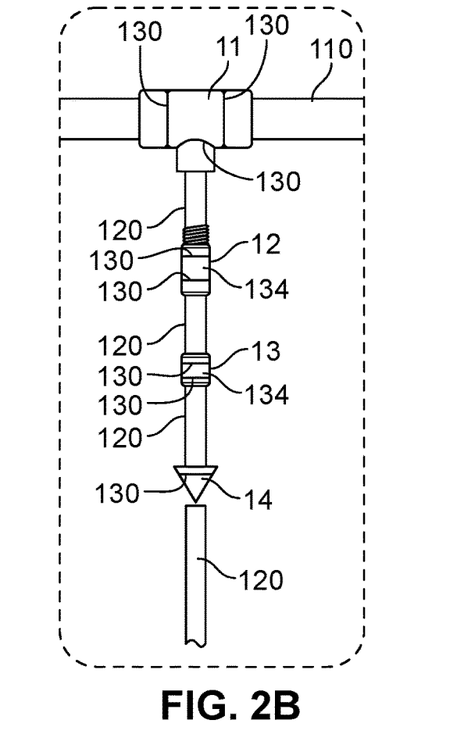
FIG. 2B is a front sectional view, illustrating a singular loop, T-joint, fluid plumbing line, connecting joints, and fitting of a prior art dialysis wall box.

For purposes of comparing wall box 100 to a typical prior art wall box 10, FIGS. 2A and 2B show front elevational views of the prior art wall box 10 illustrating T-joint 11, main valve 12, box valve 13, and quick disconnect valve 14 of a typical prior art dialysis wall box 10. Loops 110, plumbing lines 120 (e.g., pipes), joints 130 (i.e., fitting and plumbing line connection points), fittings 134, and dialysis machine drain plumbing line 304 may be, but are not necessarily, common to both prior art wall boxes 10 and wall box 100 in accordance with an embodiment of the present disclosure.

In view of FIGS. 2A and 2B, eight joints 130 (excluding wall box 10 building drain line 15 and dialysis machine drain line 304 which are not shown) at fitting and plumbing line connection points for T-joint 11, main valve 12, box valve 13, and quick disconnect valve 14 are created in the exemplary prior art wall box 10. Specifically, loop 110, at two points, and a plumbing line 120, at one point, connect to a T-Joint 11 creating three joints 130. Main valve 12 has two connection points to separate plumbing lines 120, box valve 13 has two connection points to separate plumbing lines 120, and quick disconnect 14 has one connection point to a single plumbing line 120.

Figure 2C:
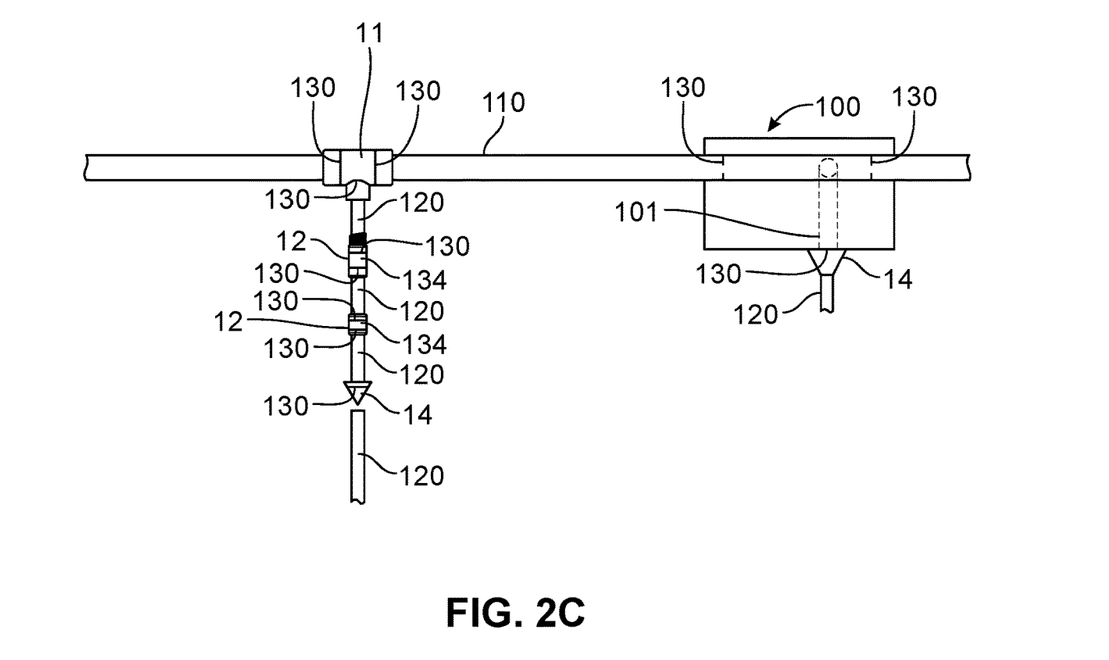
FIG. 2C is a front sectional view, showing an example of typical plumbing connections to a prior art wall box, and a wall box in accordance with an embodiment of the present disclosure, side-by-side, respectively.

FIG. 2C shows a side-by-side view of prior art wall box 10, and wall box 100 according to an exemplary embodiment of the present disclosure. Wall box 100, advantageously, eliminates the requirement for a T-Joint 11, main valve 12, and box valve 13 thereby reducing the number of system components and associated joints 130 by, at least, five joints 130 per connected loop 110.

Figure 3A:
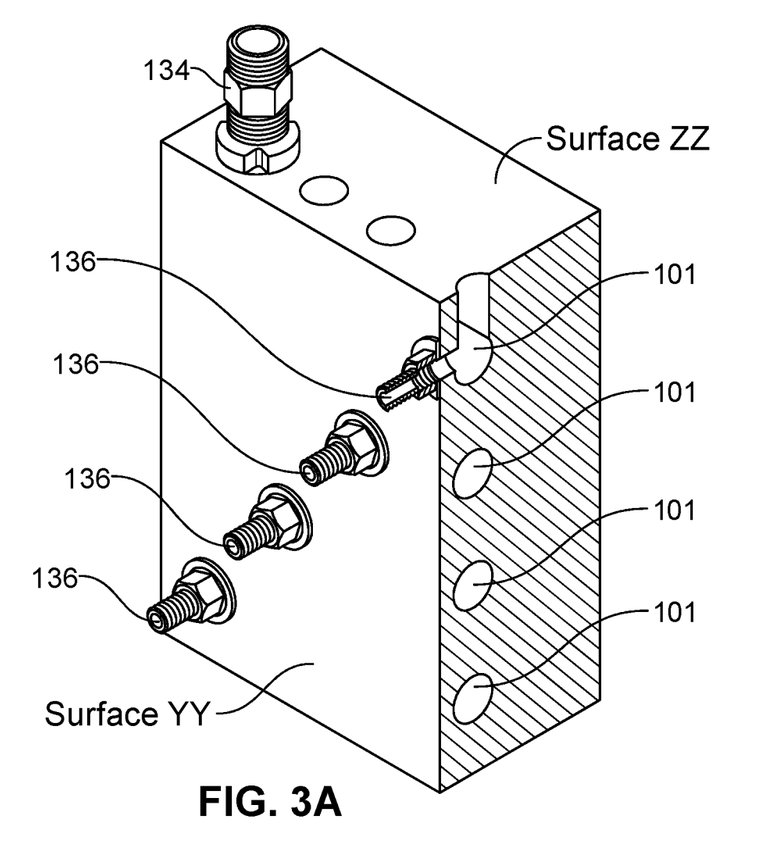
FIGS. 3A-3C are perspective and elevation views showing plumbing, fixture connection surfaces, and internal fluid flow conduits of a wall box apparatus, in accordance with an embodiment of the present disclosure.
Figure 3B:
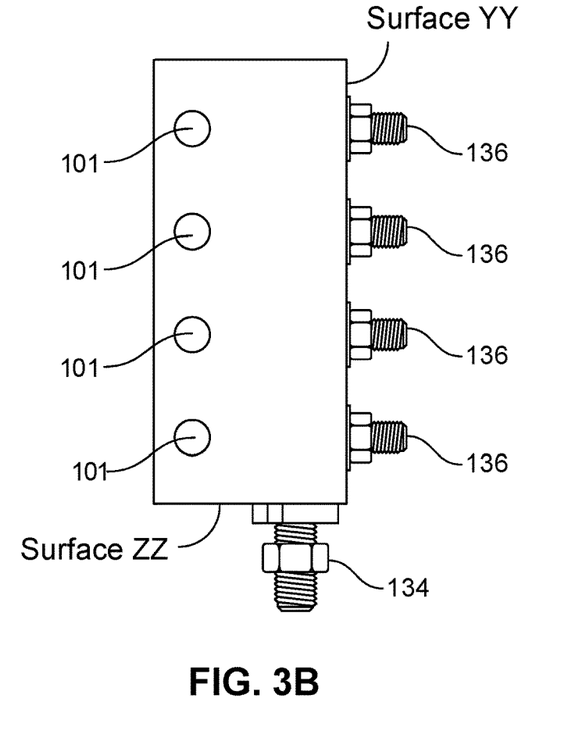
Figure 3C:
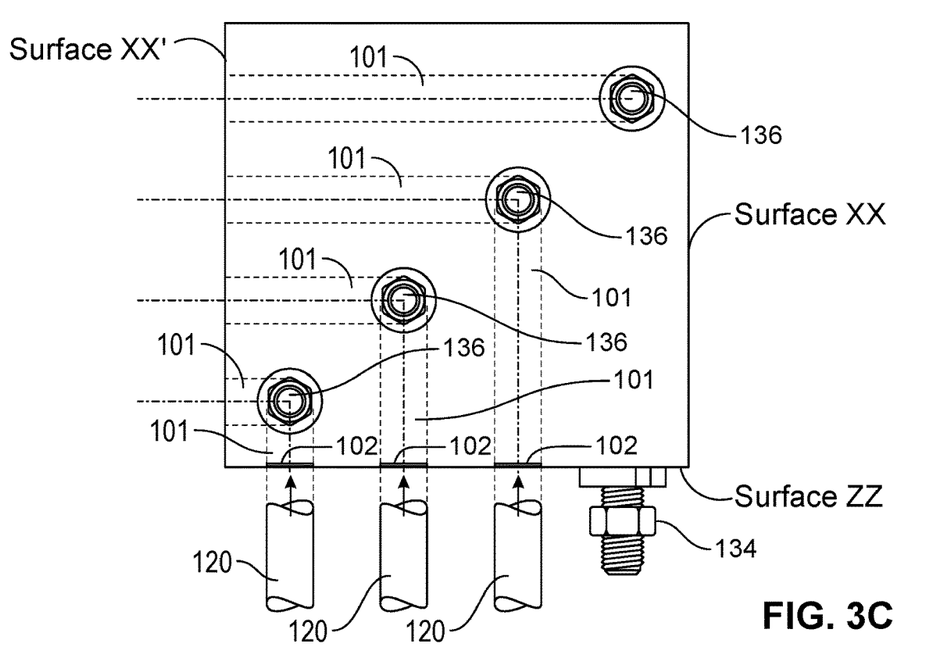

FIGS. 3A-3C show perspective and elevation views of the wall box 100, according to an embodiment of the present disclosure. At surfaces XX, XX', YY, and ZZ, exemplary fluid flow conduits 101 are configured with a connecting port 102 for receiving loops 110, plumbing lines 120, and/or plumbing fittings 134, such as valves. Fluid flow conduits 101 are configured to form connecting channels inside wall box 100 for allowing fluid flow communication between loops 110, valves 136, plumbing fittings 134, and plumbing lines 120.

According to an embodiment of the present disclosure, fluid flow conduits 101 terminate at connecting ports 102 at surfaces XX, XX', YY, and ZZ. In particular, FIGS. 1A and 3C illustrate exemplary wall box 100 configured with connecting ports 102 at surfaces XX and XX' for connecting to loops 110. In the exemplary embodiment, loops 110 enter wall box 100 at surface XX' and exit at surface XX. Within wall box 100, each loop 110 interconnects (intersects) with a respective fluid flow conduit 101 which is in fluid flow communication with a control valve 136 that modulates the flow of fluid into a respective fluid flow conduit 101 that routes fluid flow to a respective plumbing line 120. The number of loops 110 entering wall box 100 and interconnecting with respective fluid flow conduits 101 depends upon the number and types of fluids to be delivered to a hemodialysis station. It is contemplated, according to the exemplary embodiment of a wall box 100 that all loops 110, even if connected to wall box 100, may not be used for fluid transfer to a hemodialysis station. Furthermore, fluid flow to plumbing lines 120 entering a hemodialysis machine may be restricted or otherwise modulated by a respective valve 136.

Figure 4:
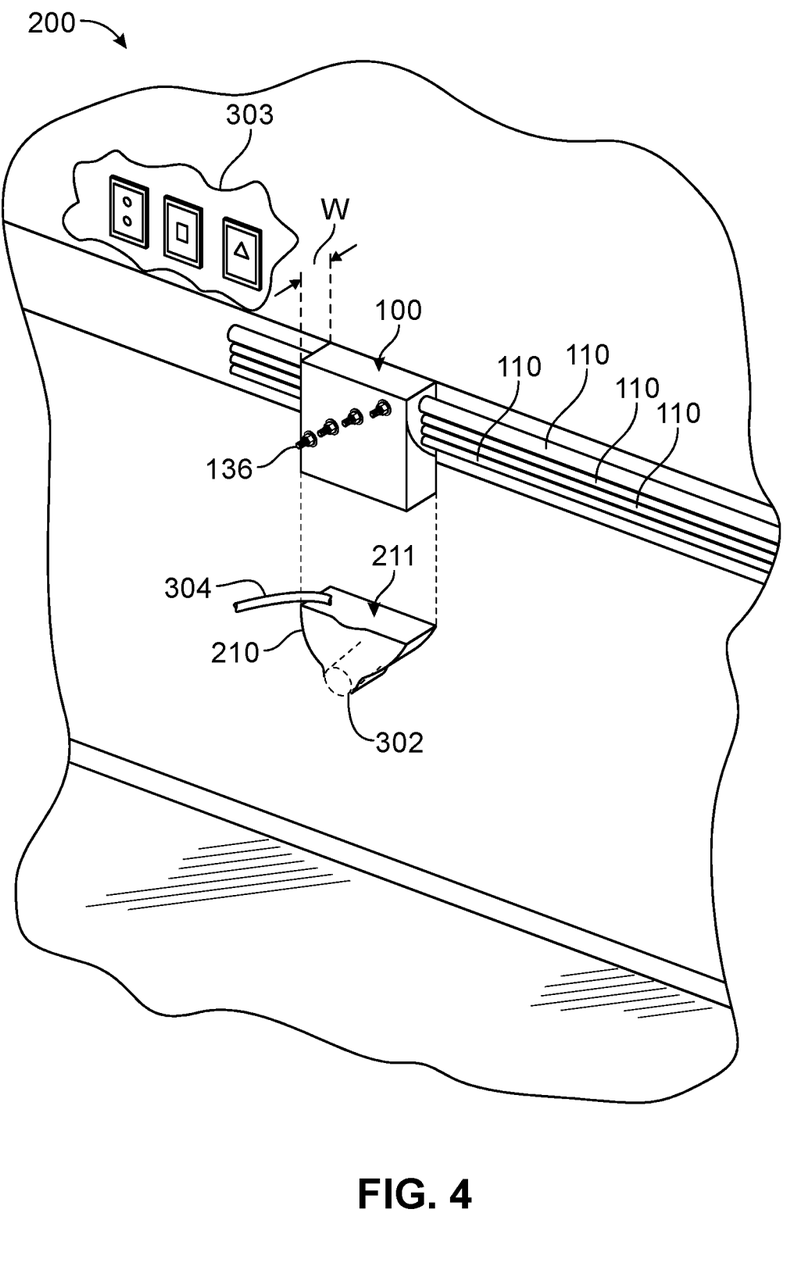
FIG. 4 is a perspective view of a wall chase system illustrating an installed wall box apparatus, in accordance with an embodiment of the present disclosure.

According to an embodiment of the present disclosure, FIG. 4 illustrates a partial view of a wall chase system 200, and demonstrates a manner in which exemplary wall box 100 would be assembled as part of the wall chase system 200 in a dialysis treatment facility. The wall box 100 is attached to a building wall 301 using screws, glue, or other attachment means (not shown). A funnel means 210, separate of the wall box 100, allows flexibility in locating the funnel means 210 for access to a buildings waste drain line 302. Funnel means 210 is located on building wall 301 generally perpendicularly below surface ZZ of wall box 100 and has a catch 211 at its top end for capturing leaks from wall box 100. The funnel means 210 may be constructed of any size and be located at any proximity, generally perpendicularly, to wall box 100 to accommodate capture of leaks and/or for cosmetic reasons. Funnel means 210 has a fitting 134 (e.g., screw, latch, hook, etc. [not shown]) for holding a kidney-dialysis machine's drain plumb line 304 within the catch 211 of the funnel means 210 to channel dialysis machine waste directly to a facility's waste drain line 302.

Figure 5:
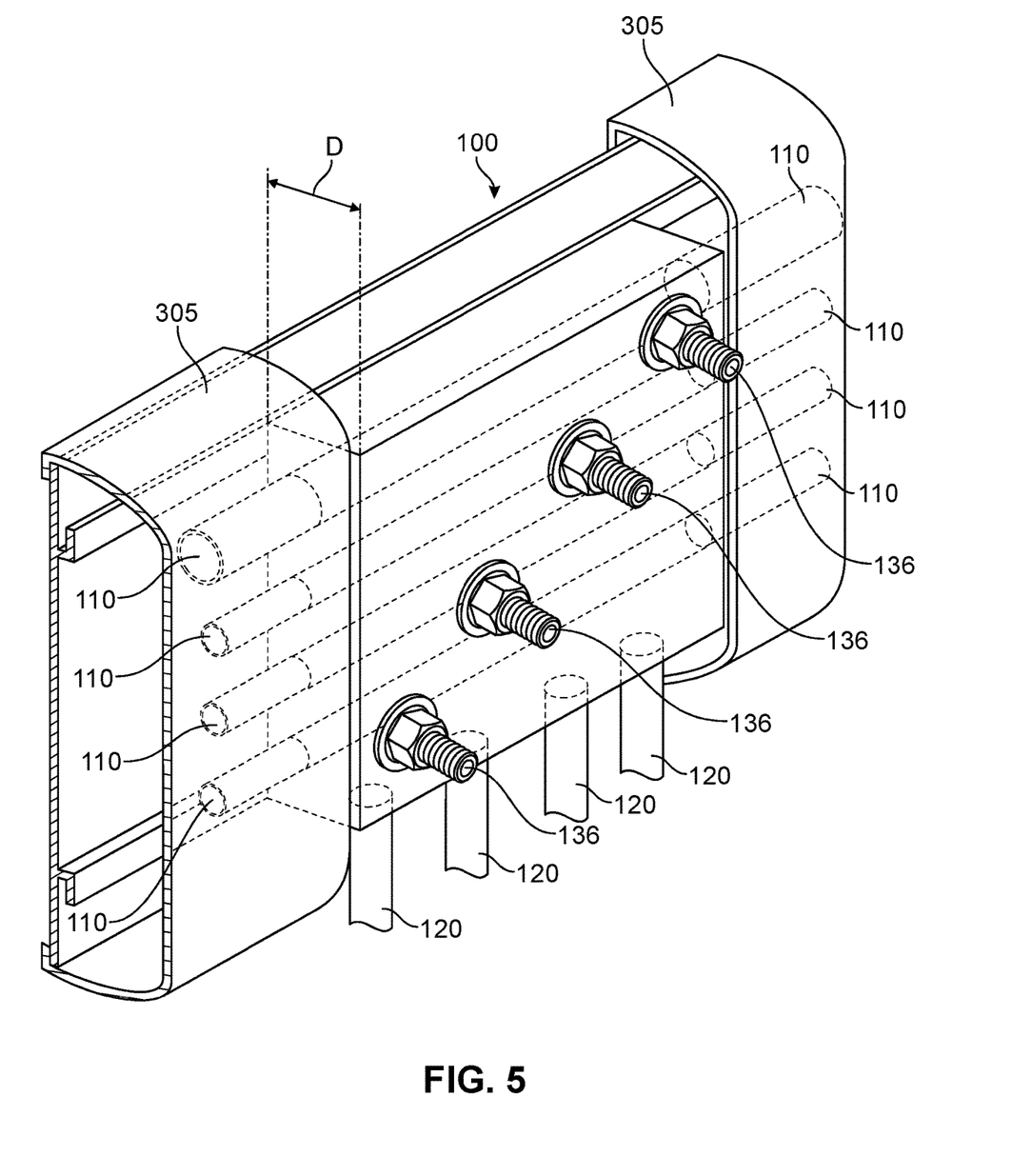
FIG. 5 is a perspective sectional view of a wall chase system showing wall box and bumper rail covering, in accordance with an embodiment of the present invention.

FIG. 4 shows wall box 100, assembled on a building wall 301, extending from building wall 301 a width "W". Width W, in accordance with an embodiment of the present disclosure, is about three inches. Additionally, in an embodiment of the present disclosure, assembly of a building structure's electrical connections, data lines, and the like within, or within close proximity to, a wall chase system 200 is eliminated. Advantageously, such utilities (e.g., electrical connections, data lines, and the like) 303 may be located elsewhere on wall 301, thereby removing fluid lines of a building and/or a wall box, as generally constructed in the prior art, from proximity to them. Plumbing lines, such as loops 110, connected to wall box 100, generally run along wall 301, and may be concealed by a bumper guard rail 305 of sufficient width to conceal loops 110 as illustrated in FIG. 5.

Figure 6:
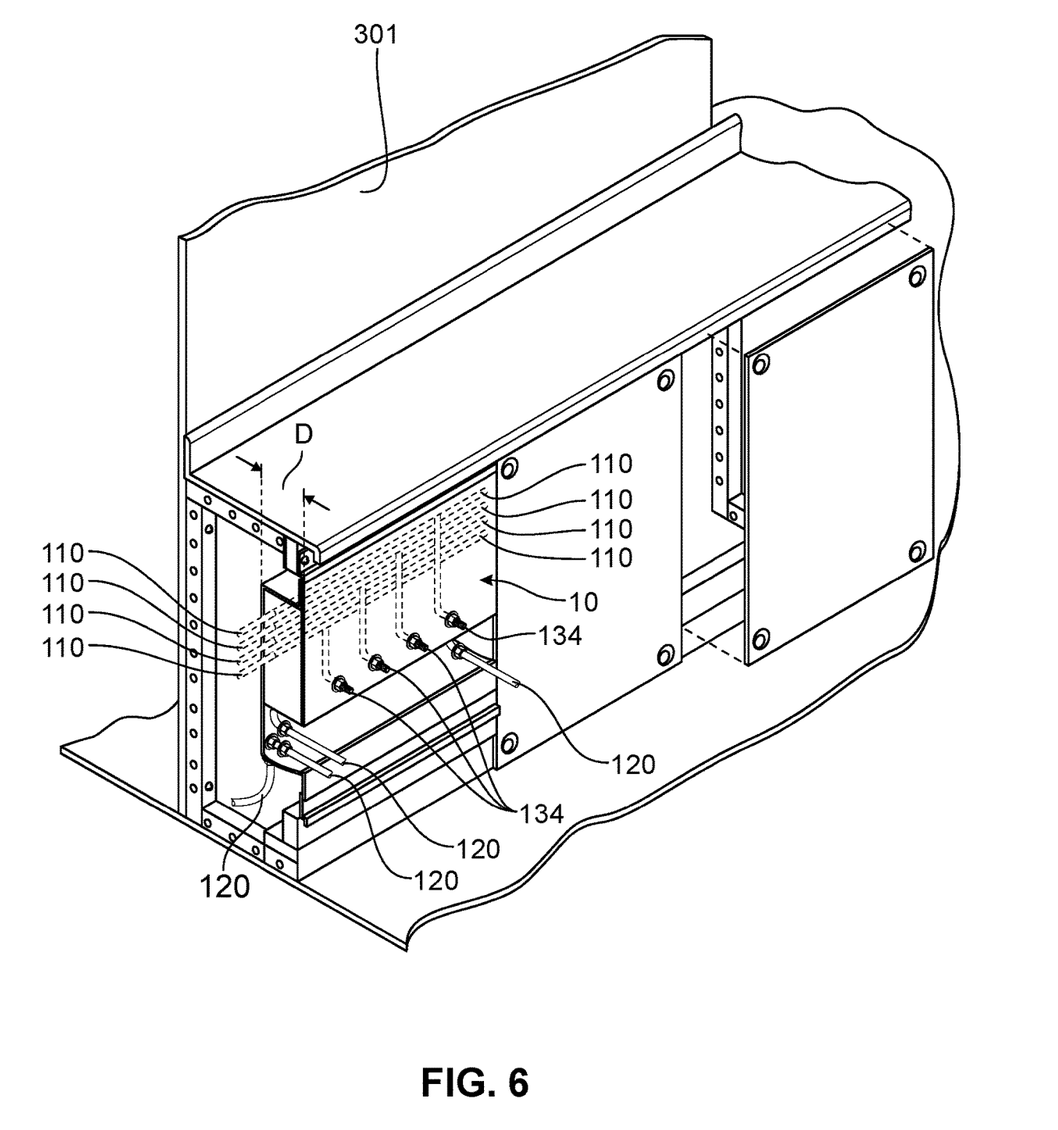
FIG. 6 is a sectional view illustrating a prior art chase wall system configured with a prior art dialysis wall box.

FIG. 6 shows a sectional view of a typical prior art wall chase system 20, including a prior art wall box 10 of width D (i.e., at least eighteen inches according to prior art reference U.S. Pat. No. 9,421,312 to Marinan), assembled therein. The exemplary prior art wall chase system 20 has mounted therein and/or thereon plumbing lines 120, fittings 134, electrical-supply and data elements 303 (not shown). Exemplary prior art wall chase system 20 extends substantially more from a treatment facility's wall 301 as compared to wall chase 200 in accordance with an embodiment of the present disclosure. Wall chase system 20 requires about, at least, nine square feet of floor space and about, at least, twenty-four cubic feet of a treatment facility's room volume per kidney-dialysis treatment station.

Thus, it is seen, in accordance with the disclosure herein and the accompanying drawings, that the at least one embodiment of the wall box 100 and wall chase system 200 provides more reliable infection control, by eliminating joints, while also reducing the amount of space required for a wall chase system in a kidney-dialysis treatment facility. Furthermore, the wall box 100 has an additional advantage in that it simplifies fluid transport for enhanced reliability by reducing the number of plumbing lines and fittings. In an exemplary embodiment, it is contemplated that wall box 100 may be configured as an interface panel (comprising plumbing lines, fittings, valves, etc.) closely and directly mounted to a facility wall that provides connections to building and kidney-dialysis machine plumbing lines.

Those skilled in the art would appreciate that features (e.g., connection ports, fittings, valves, etc.) on all surfaces of wall box 100 are interchangeable with adjoining and/or opposite surfaces without loss of functionality (e.g., loops 110 may be located on Surface YY, valve fittings 136 on Surface ZZ, and connecting ports 102 for plumbing lines 120 on Surface XX or XX'). Relocation of features in such a manner would be done, for example, to accommodate treatment facility available space and configuration constraints.

While the above description contains many specificities, these should not be construed as limitations on the scope, but rather as an exemplification of one embodiment thereof. It should be understood that the broadest scope of this invention includes modifications such as diverse shapes, sizes, and materials. Accordingly, the scope of the present invention should be determined, not by the embodiments illustrated, but by the appended claims and their legal equivalents.

DRAWINGS—LIST OF ELEMENTS AND REFERENCE NUMERALS 10 prior art wall box
11 T-joint
12 main valve
13 box valve
14 quick disconnect valve
15 building drain line
20 prior art wall chase system
100 wall box
101 fluid flow conduit
102 connecting ports
110 loops
120 plumbing line
130 joint
134 fitting
136 flow control valve
200 wall chase system
210 funnel means
211 funnel catch
301 building interior wall
302 building waste drain line
303 building utilities (e.g., electrical connections, data lines, etc.)
304 dialysis machine drain plumb line
305 bumper guard rail
D minimum prior art wall chase system offset from facility interior wall
T minimum wall box wall thickness
W maximum width of wall box

What is claimed is:

1. A dialysis treatment facility wall box comprising:
a solid block housing having a plurality of surfaces that define an enclosure;
a plurality of fluid flow conduits interconnected within the housing, said plurality of fluid flow conduits configured to accommodate fluid flow control and communication between a plurality of fluid sources in a dialysis treatment facility; and
a plurality of connecting ports configured at the terminus of said plurality of conduits, respectively, at the plurality of said surfaces for connecting to dialysis treatment facility loops and/or kidney-dialysis machines.

2. The wall box of claim 1, wherein said housing has a plurality of said plurality of connecting ports configured on a plurality of conduits, respectively, said connecting ports terminating on the said plurality of surfaces of said housing.

3. The wall box of claim 1, wherein said connecting ports, having a predetermined cross-sectional shape, and forming a hole adjacent a plane of one of said plurality of surfaces provides sufficient thickness to retain fluid pressure with respect to a said plane of one or more of a said plurality of surfaces.

4. The wall box of claim 3, wherein one or more of said plurality of connecting ports are counterbored with respect to a conduit located on any of said plurality of surfaces.

5. A dialysis support system in a dialysis treatment facility having plumbing lines therein for use with at least one dialysis machine, having plumbing lines connected thereto in the facility, said support system designed to be mounted to a wall of a building or facility comprising:
one or more dialysis machines positioned at predetermined locations in the treatment facility;
a wall box comprised of:
a solid block housing,
a top side surface,
a bottom side surface,
a front side surface,
a rear side surface,
a left side surface,
a right side surface,
a plurality of fluid flow conduits interconnected within the wall box and configured to accommodate fluid flow communication between a plurality of fluid sources,
a plurality connecting ports fashioned on terminus of said conduits at the plurality of said surfaces, and
a chase system attached to facility wall having means for containing the wall box and/or facility plumbing lines.

6. The system of claim 5, wherein the wall box, at a left side surface and a right side surface of said wall box, is in fluid flow communication with said facility plumbing lines through one or more of said plurality of conduits.

7. The system of claim 6, wherein the wall box, at a left side surface and a right side surface of said wall box is in fluid flow communication with said facility plumbing lines via one or more of said connecting ports fashioned on terminus of one or more of said conduits.

8. The system of claim 5, wherein the wall box, at a front side surface and/or a bottom side surface of said wall box, is in fluid flow communication with said dialysis machine plumbing lines.

9. The system of claim 8, wherein the wall box, at a front side surface and/or a bottom side surface of said wall box, is in fluid flow communication with said dialysis machine plumbing lines via one or more of said connecting ports fashioned on terminus of one or more of said conduits.

10. The system of claim 5, wherein one or more of the plurality of conduits or one or more of the plurality of connecting ports include a fitting.

11. The system of claim 5, wherein a funnel means is attached to the facility wall, said funnel means being generally perpendicularly aligned below the bottom side surface of the wall box for capturing waste from the wall box and from said dialysis machine plumbing lines.

12. The system of claim 5, wherein the top side, bottom side, front side, rear side, left side, and right side of said wall box are interchangeable.

13. The system of claim 5, wherein the wall box is configured to provide concurrent fluid flow communication to a plurality of dialysis machines on opposite sides of a facility wall.

14. A method for transporting fluid flow through a building plumbing line and one or more kidney-dialysis machines plumbing lines, said building and said kidney-dialysis machines in fluid communication with a wall box, the method comprising:
providing a wall box having a plurality of surfaces that define an enclosure;
fashioning a plurality of fluid flow conduits interconnected within the wall box, said plurality of fluid flow conduits configured to accommodate fluid communication between said building and said kidney-dialysis machines; and producing connecting ports on terminus of said conduits at a top side surface, a bottom side surface, a front side surface, a rear side surface, a left side surface, and a right side surface of said wall box for establishing fluid communication with said plumbing lines.

15. The method of claim 14, wherein establishing fluid communication with said building plumbing lines and said kidney-dialysis machines plumbing lines comprises:
  connecting a building plumbing line to said connecting port on the left side surface or the right side surface of said wall box;
  connecting a building plumbing line to said connecting port on the opposite side of said wall box, wherein said connecting port on the left side surface or the right side surface of said wall box is interconnected via a common fluid flow conduit with said connecting port on the opposite side of wall box;
  connecting a kidney-dialysis machine plumbing line to said connecting port on the front side surface or the bottom side surface of said wall box;
  connecting a kidney-dialysis machine plumbing line to a connecting port on the bottom side surface or the front side surface of said wall box, wherein said connecting port on the front side surface or the bottom side surface of said wall box is interconnected via a common fluid flow conduit with said connecting port on the right side or left side, commonly connected with a fluid flow conduit, of wall box.

16. The method of claim 14, wherein said wall box provides a means for reducing the number of joints in plumbing systems.

17. The method of claim 14, wherein said wall box provides a means for increasing available space in a building, said means comprising.

18. The method of claim 14, wherein said wall box provides a means for improving safety, reducing leaks, and reducing need for disinfection said.

19. A method for transporting fluid flow through a dialysis treatment facility plumbing lines and one or more kidney-dialysis machines plumbing lines, said dialysis treatment facility and said kidney-dialysis machines in fluid communication with said wall box, the method comprising:
  providing a wall box having a plurality of surfaces that define an enclosure;
  fashioning a plurality of fluid flow conduits interconnected within the wall box, said plurality of fluid flow conduits configured to accommodate fluid communication between said building and said kidney-dialysis machines; and
  producing connecting ports on terminus of said conduits at a top side surface, a bottom side surface, a front side surface, a rear side surface, a left side surface, and a right side surface of said wall box for establishing fluid communication with said plumbing lines.

20. The method of claim 19, wherein establishing fluid communication with said dialysis treatment facility plumbing lines and said kidney-dialysis machines plumbing lines comprises:
  connecting a dialysis treatment facility plumbing line to said connecting port on the left side surface or the right side surface of said wall box;
  connecting a dialysis treatment facility plumbing line to said connecting port on the opposite side of said wall box, wherein said connecting port on the left side surface or the right side surface of said wall box is interconnected via a common fluid flow conduit with said connecting port on the opposite side of wall box;
  connecting a kidney-dialysis machine plumbing line to said connecting port on the front side surface or the bottom side surface of said wall box;
  connecting a kidney-dialysis machine plumbing line to a connecting port on the bottom side surface or the front side surface of said wall box, wherein said connecting port on the front side surface or the bottom side surface of said wall box is interconnected via a common fluid flow conduit with said connecting port on the right side or left side, commonly connected with a fluid flow conduit, of wall box.

21. The method of claim 19, wherein said wall box provides a means for reducing the number of joints in plumbing systems.

22. The method of claim 19, wherein said wall box provides a means for increasing available space in a dialysis treatment facility, said means comprising the elimination and/or reduction of shelving and cabinetry used in said dialysis treatment facility.

23. The method of claim 19, wherein said wall box provides a means for improving safety, reducing leaks, and reducing infection stemming from a dialysis treatment facility operation.

* * * * *